(12) United States Patent
Paffhausen et al.

(10) Patent No.: US 6,191,852 B1
(45) Date of Patent: *Feb. 20, 2001

(54) OPTICAL MEASUREMENT SYSTEM FOR DETECTING LUMINESCENCE OR FLUORESCENCE SIGNALS

(75) Inventors: Wolfgang Paffhausen, Leverkusen; Martin Bechem, Wuppertal, both of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/170,482

(22) Filed: Oct. 13, 1998

(30) Foreign Application Priority Data

Oct. 14, 1997 (DE) .................................. 197 45 373

(51) Int. Cl.[7] .................................................. G01N 21/01
(52) U.S. Cl. .................................... 356/244; 356/422
(58) Field of Search .............................. 356/311, 422, 356/244, 418, 419

(56) References Cited

U.S. PATENT DOCUMENTS

| 3,101,411 | 8/1963 | Richards | 250/83.3 |
|---|---|---|---|
| 4,108,794 | 8/1978 | Yonekubo | 252/408 |
| 4,554,839 | 11/1985 | Hewett et al. | 73/864 |
| 4,922,092 | 5/1990 | Rushbrooke et al. | 250/213 |
| 5,096,835 | 3/1992 | Yokomori et al. | 436/165 |
| 5,347,122 | 9/1994 | Ansorge | 250/227.11 |
| 5,508,200 | 4/1996 | Tiffany et al. | 436/44 |
| 5,635,402 | 6/1997 | Alfano et al. | 436/63 |
| 5,686,723 | 11/1997 | Devenyi et al. | 250/227.11 |

FOREIGN PATENT DOCUMENTS

| 2606064 | 9/1976 | (DE) | G02B/21/00 |
|---|---|---|---|
| 3833064 | 4/1990 | (DE) | G01N/35/00 |
| 3841961 | 6/1990 | (DE) | G01N/35/00 |

(List continued on next page.)

OTHER PUBLICATIONS

Sharonov, S. et al. : Confocal spectral imaging analysis in studies of the spatial distribution of antitumour drugs within living cancer cells. In: Analytica Chimica Acta, 290, 1994, pp. 40–47.

Wittrup, K.D. et al.: Fluorescence Array Detector for Large-Field Quantitative Fluorescence Cytometry. In: Cytometry, vol. 16, 1994, pp. 206–213.

(List continued on next page.)

Primary Examiner—Frank G. Font
Assistant Examiner—Reginald A. Ratliff
(74) Attorney, Agent, or Firm—Norris McLaughlin & Marcus P.A.

(57) ABSTRACT

In the measurement system for detecting optical signals of microassays, the signal-generating test objects 5 are arranged on an investigation surface of a planar carrier 4. The planar carrier 4 is, in particular, a microtitre plate for biological objects. In principle, the measurement system comprises an optical imaging arrangement which reduces the size of the test objects 4 to be measured in such a way that all the objects are imaged completely on a two-dimensional, photosensitive image sensor 6. For imaging, a high-resolution glass-fiber taper element 1 having a large-area 2 and a small-area end 3 is used in this case, whose end surfaces 2, 3 are selected such that the large-area end surface 2 corresponds at least to the investigation surface of the carrier 4 and the small-area end surface 3 corresponds to the size of the image sensor 6, the ratio of the end surfaces 2, 3 producing the scale of reduction of the optical imaging arrangement in order to image the investigation surface of the carrier 4 completely onto the image sensor 6.

9 Claims, 7 Drawing Sheets

U.S. PATENT DOCUMENTS

| | | | |
|---|---|---|---|
| 4015930 | 11/1990 | (DE) | G01N/15/02 |
| 4313603 | 10/1993 | (DE) | G01N/35/00 |
| 19714725 | 10/1997 | (DE) | G01J/1/04 |
| 0025350 | 3/1981 | (EP) | G01N/21/76 |
| 0266881 | 5/1988 | (EP) | G01N/21/64 |
| 0545673 | 6/1993 | (EP) | B01L/7/02 |
| 2315131 | 1/1998 | (GB) | G02B/6/04 |
| 9109300 | 6/1991 | (WO) | G01N/21/76 |
| 9739329 | 10/1997 | (WO) | G01N/1/28 |
| 9823945 | 6/1998 | (WO) | G01N/21/77 |

OTHER PUBLICATIONS

Schott Fiber Optics: Fused Fiber Optic Tapers, sales brochure consisting of 8 pages (Nov. 1995).

INCOM sales brochure re: Fiber Optic Technology, consisting of 6 pages.

Patent Abstracts of Japan, abstract of JP 63298137 (Dec. 5, 1998).

English–language translation of abstract of DE 43 13 603.

English–language translation of abstract of DE 38 41 961.

English–language translation of abstract of DE 38 33 064.

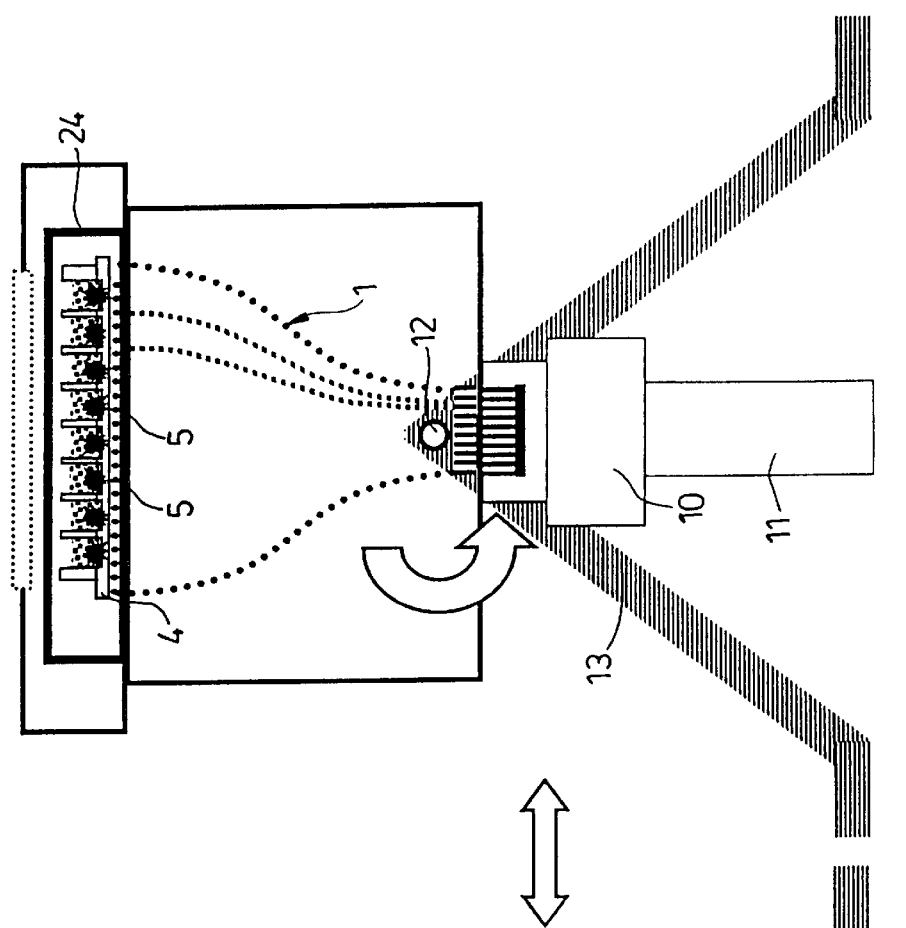
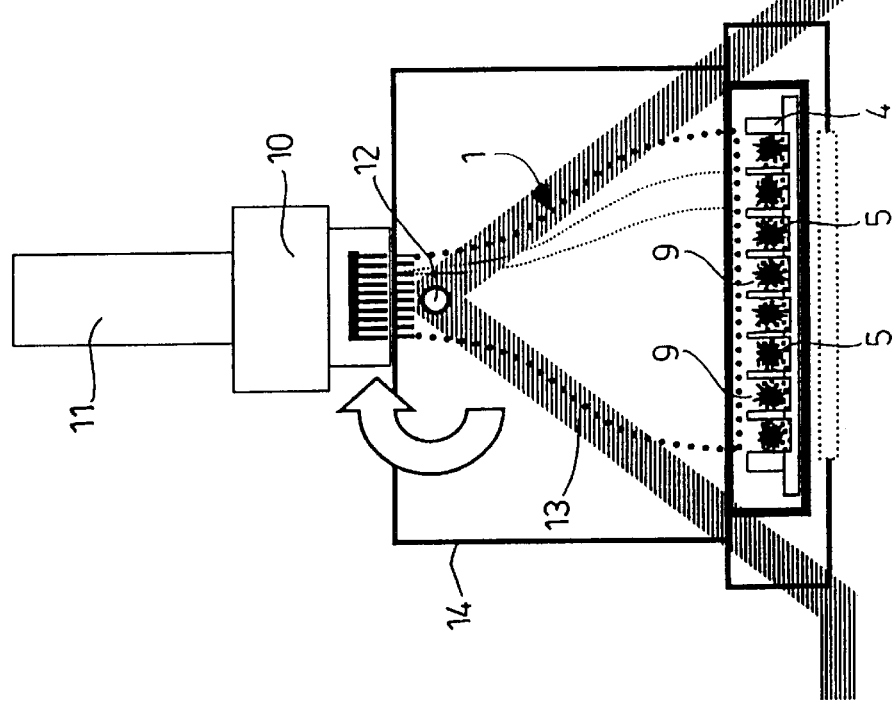
Fig. 2a
Fig. 2b

OPTICAL MEASUREMENT SYSTEM FOR DETECTING LUMINESCENCE OR FLUORESCENCE SIGNALS

The invention is based on a measurement system for detecting optical signals of microassays, in which the signal-generating test objects are arranged on an investigation surface of a planar carrier, comprising an optical imaging arrangements which reduces the size of the test objects to be measured in such a way, that all the objects are imaged completely on a two-dimensional, photosensitive image sensor. The optical signals are converted by the image sensor into electronic image signals, which are evaluated by a measurement computer in a known manner and processed further.

"Test objects" in the context of the invention are to be understood to mean fluorescent or luminescent and/or fluorescent- or luminescent-marked samples which are provided on the carrier or in microtitre plates and in which a chemoluminescent or bioluminescent reaction proceeds in the case of luminescence on account of molecular interactions, in which reaction photons can be liberated and detected, or fluorescence arises in the case of fluorescence on account of the interaction of a fluorescent die with which the objects are marked, given irradiation by suitable excitation energy, with the result that photons can be liberated and detected. The samples themselves may be present in the form of dissolved chemical components or else in the form of biological test systems, such as for instance, in the case of enzymatic reactions, antigen-antibody couplings, protein binding assays, ligands-receptor interactions or receptor assays. In this case, the biological test system may be configured as a cellular assay (adherent or suspension cells, primarily mammalian cells, but also plant cells, bacteria, fungi, yeasts or viruses) or else may comprise subcellular constituents, such as e.g. isolated cell nuclei or cytoplasm agglomerates, or else may comprise artificial carriers, such as e.g. plastic beads or glass microspheres, on which biologically active material, generally cellular or subcellular constituents, has been applied, an optical signal in the form of photons being liberated as a result of the interaction of different components.

A problem that frequently arises in the measurement of luminescence or fluorescence in biomedical assays is, that the optical signals correlated with the biological interaction are generally small enough that bioluminescent or biofluorescent events can usually be detected only using photomultipliers (light intensifiers). In the limit range of detectability, it is necessary to use luminescence measurement systems (photon counting systems).

If the intention is for e.g. microtitre plates (MTP) having dimensions of approximately 130 mm×86 mm, depth approximately 10–14 mm, which contain 96, 384 or 1536 test holes, to be optically measured simultaneously using imaging methods, then two-dimensional luminescence measurement systems are necessary for this. The prior art in this context is to image the MTP by means of an optical lens arrangement onto the photocathode of an image intensifier (entry window) and to amplify the impinging photons after photoelectric conversion as photoelectrons in a microchannel plate (MCP=multichannel plate). At the exit window of the MCP, the multiplied electrons impinge on a luminescent phosphor, where they engender, in a spatially resolved manner, a light signal which is amplified by up to 1,000,000 times relative to the input and can be detected, in a spatially resolved manner, using a CCD sensor.

An output image, that has been intensified in such a way, can be evaluated with the aid of image-processing processes, the brightness in each hole of a microtitre plate being calculated as the number of recorded photon events. Corresponding systems are commercially available as so-called MTP readers from various companies. If the intensities are sufficiently high and the integration time is unimportant, it is also possible to have recourse to commercially available cooled CCD systems instead of the image intensifier.

By comparing different luminescence measurement systems from various manufacturers, it was possible to demonstrate that photons, which generate an electron on the photocathode, can be detected by the known luminescence measurement systems having single- or two-stage amplification. A higher level of amplification after photoelectric conversion, and that is to say downstream of the photocathode, does not lead to an increase in the system sensitivity.

An increase in sensitivity on the basis of a higher quantum yield of the photocathode of an image intensifier is theoretically possible. However, physical limits and the absence of corresponding commercial detectors afford no technically realisable solution at the present time.

In order to image an object, the microtitre plate in the case described here, onto the photocathode of an image intensifier, all the manufacturers use an objective of high light-gathering power. Some manufacturers use standard photo objectives, others use specially corrected objectives having a high f-number. The best high-performance objectives used to date already have a very high light intensity with an aperture ratio of approximately 1:1.0 and a focal length of 50 mm. An optical arrangement having a significantly higher light-gathering power cannot be constructed for physical reasons.

Owing to the three-dimensional nature of the microtitre plate with its holes having a depth of approximately 10–14 mm, in the case of conventional optical imaging it is necessary to observe an object distance of approximately 70 cm (distance: MTP from image sensor) owing to the geometric vignetting that occurs at the edge holes. A housing in which the microtitre plate and the detection system are integrated in a completely light-tight manner for the luminescence measurement system must be correspondingly high. This geometrical distance r between light origination and detector has a particular disadvantageous effect with regard to the system sensitivity since the intensity decreases at $I/r^2$. The light quantum originating statistically in a hole of the microtitre plate leaves the hole diffusely, with the result that it is possible to detect, purely geometrically, only a fraction (surface of the hemisphere with a radius of 70 cm in relation to the aperture of the objective with a diameter of 5 cm) of a few thousandths. No fundamental improvement in the system sensitivity can be achieved with conventional optical imaging arrangements such as lens systems or else mirror systems.

In order to ensure a high sample throughput in an acceptable time in the event of screening biological test systems with optical signal processing during a test of a few 100,000 substances, it is necessary to resort to imaging methods owing to the advantage of parallel processing, e.g. in microtitre plates. Owing to the low luminous intensity of the bioluminescent or biofluorescent reactions, integration times of a few minutes are frequently necessary for a statistically secure signal/noise ratio in the photon counting mode.

In order to increase e.g. the capacity of a robot installation for the investigation of luminescence or fluorescence signals in microtitre plates by reducing the integration time for the measurement of microtitre plates and/or to reduce e.g. the number of cells per test hole and/or to reduce the size of expensive substrate quantities for an enzyme reaction, the object consisted in increasing the sensitivity of the known luminescence or fluorescence measurement systems.

In the case of an optical measurement system having an optical imaging arrangement for the test objects to be measured, which test objects are situated on the investigation surface of the carrier, and a two-dimensional, photosensitive image sensor onto which all the objects are completely imaged, this object is achieved according to the invention by the fact that the optical imaging arrangement comprises a high-resolution glass-fibre taper element having a large-area and a small-area end and the end surfaces are chosen such that the large-area end surface corresponds at least to the investigation surface of the carrier and the small-area end surface corresponds to the size of the image sensor, the ratio of the end surfaces producing the scale of reduction of the optical imaging arrangement in order to image the investigation surface of the carrier completely onto the image sensor. "High-resolution" is in this case to be understood to mean that the fibre diameter of the densely packed glass fibres situated next to one another at the large end surface of the glass-fibre taper element is $\leq 12$ $\mu$m.

The invention is preferably realised with the aid of an arrangement in which the planar carrier comprises a microtitre plate having a multiplicity of holes for receiving the signal-generating test objects, the image sensor comprises an image intensifier and a video camera for converting the intensified image signals into electronic signals, and the glass-fibre taper element is designed in such a way that a reduced image of the microtitre plate that fully fills the entry window of the image intensifier is produced.

In order to prevent light-induced long-term phosphorescence from leading to false light signals when white plastic carriers are used, use is advantageously made of an image intensifier having a bialkali photocathode whose spectral sensitivity at wavelengths>700 nm is<1% of its maximum sensitivity.

In accordance with a preferred design, the microtitre plate is provided with a horizontally movable and vertically adjustable, drawer-like mount, which, after horizontal retraction, is raised to an extent such that the large-area end of the glass-fibre taper element is in direct contact with the microtitre plate.

The small-area end of the glass-fibre taper element is advantageously in direct optical contact with the entry window of the image intensifier.

The entry window of the image intensifier with the innerly situated photocathode is advantageously furnished as a glass-fibre plate with a numerical aperture NA=1.0, in order to ensure that the image is transferred efficiently, optically and with a geometrically high resolution from the surface of the glass-fibre taper element to the photocathode of the image intensifier.

In order to minimize reflection losses, provision is furthermore made for an air gap remaining between the glass-fibre taper element and the entry window of the image intensifier to be filled with an oil film, whose refractive index corresponds to the refractive index of the taper element.

In order to investigate biofluorescent objects in a microtitre plate, the apparatus according to the invention is modified in such a way that the microtitre plate has an optically transparent base, in that the drawer-like mount is designed as a frame construction and in that a light source for fluorescence excitation which generates a light pencil of inclined incidence with respect to the optical axis is arranged underneath the microtitre plate.

A further development of the invention is characterized in that the entire apparatus can be pivoted through 180° about a horizontal spindle and has the following further features:
a) The microtitre plate has an optically transparent base.
b) The drawer-like slide mount for the microtitre plate is designed as a frame construction.
c) The measurement system additionally has a micropipetting system whose individual pipettes are assigned to the test holes in the microtitre plate.

An arrangement of this type permits in-situ observation of the luminescence of biological objects under the influence of an added reagent. This enables kinetic bioluminescence investigations which reproduce the dynamic action profile of pharmacologically active substances.

The invention affords the following advantages:
the new system is a factor of 10 more light sensitive than conventional microtitre plate luminescence measurement systems. In this way, very low-intensity bioluminescent reactions can actually be detected for the first time.

Given the same signal/noise ratio, the integration time can be shortened by the factor of 10. Alternatively, given the same signal/noise ratio, the quantity of biological objects (e.g. the cell number/microtitre plates) can be reduced by the factor 10 or conversely, given the same substrate quantity, the sample throughput can be increased by the factor of 10.

Given the same signal/noise ratio, the substrate quantity which liberates the photons to be detected in a biochemical reaction can be reduced by the factor of 10.

Given the same signal/noise ratio, owing to the high sensitivity it is possible to decrease the fluorescent die concentration by the factor of 10 (reduction of the secondary effect on the biological system) or to shorten the measurement times by the factor of 10 (reduction of the bleaching effects).

On account of the perpendicular light capture of the optical taper arrangement at the microtitre plate, vignetting effects do not occur.

On account of the small structure of the system owing to the small physical height of the optical taper arrangement of approximately 16 cm in comparison with the distance of approximately 70 cm in the case of lens imaging. it is possible to change from a surface viewing to a direct viewing measurement method without reconstruction work by means of an 180° rotation of the system through the axis of gravity.

The invention is explained in more detail below with reference to drawings and exemplary embodiments. In the figures:

FIG. 2a shows a diagrammatic view of a luminescence measurement system in the basic position (TOP position)

Figure 3:
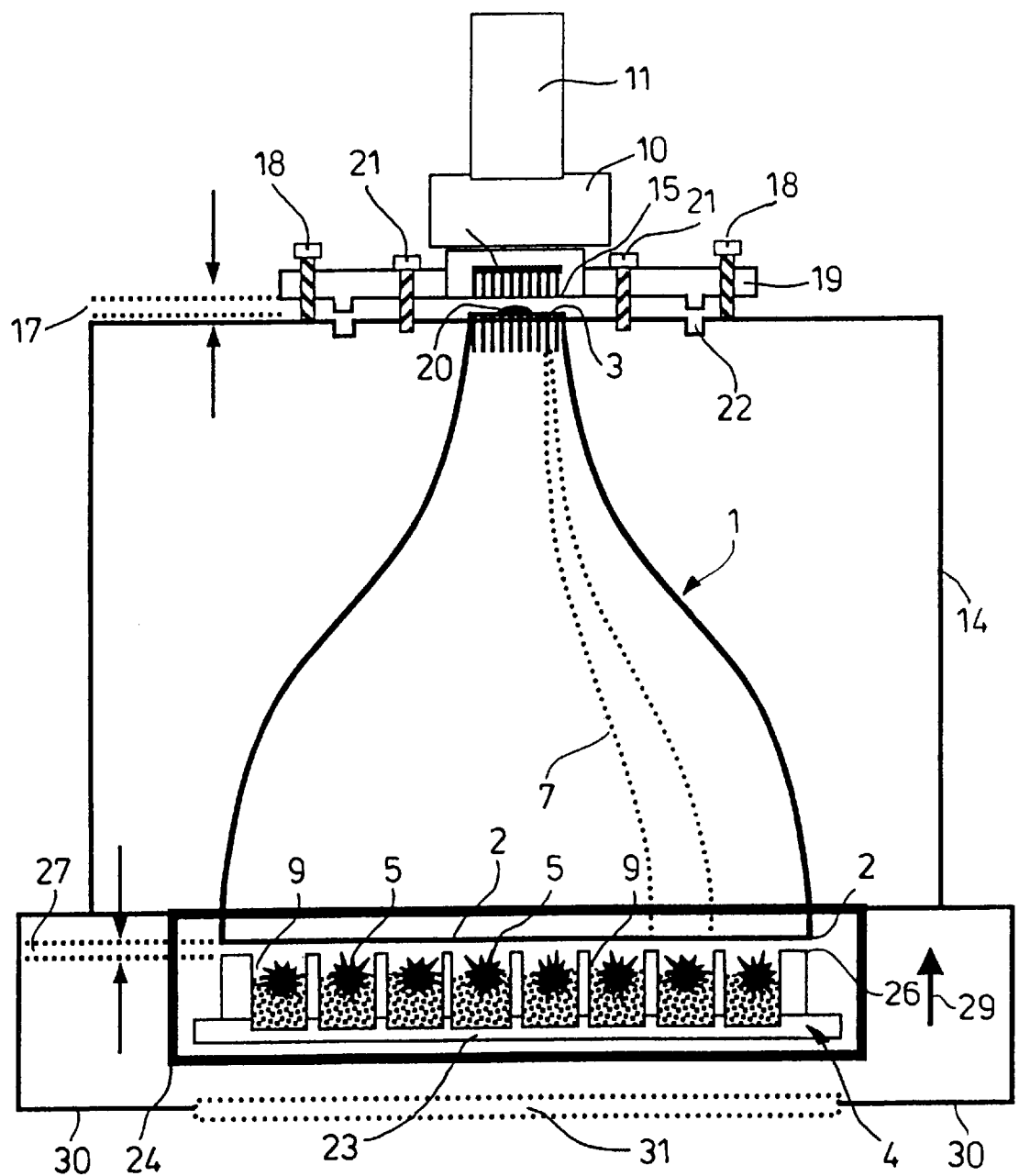
Figure 4:
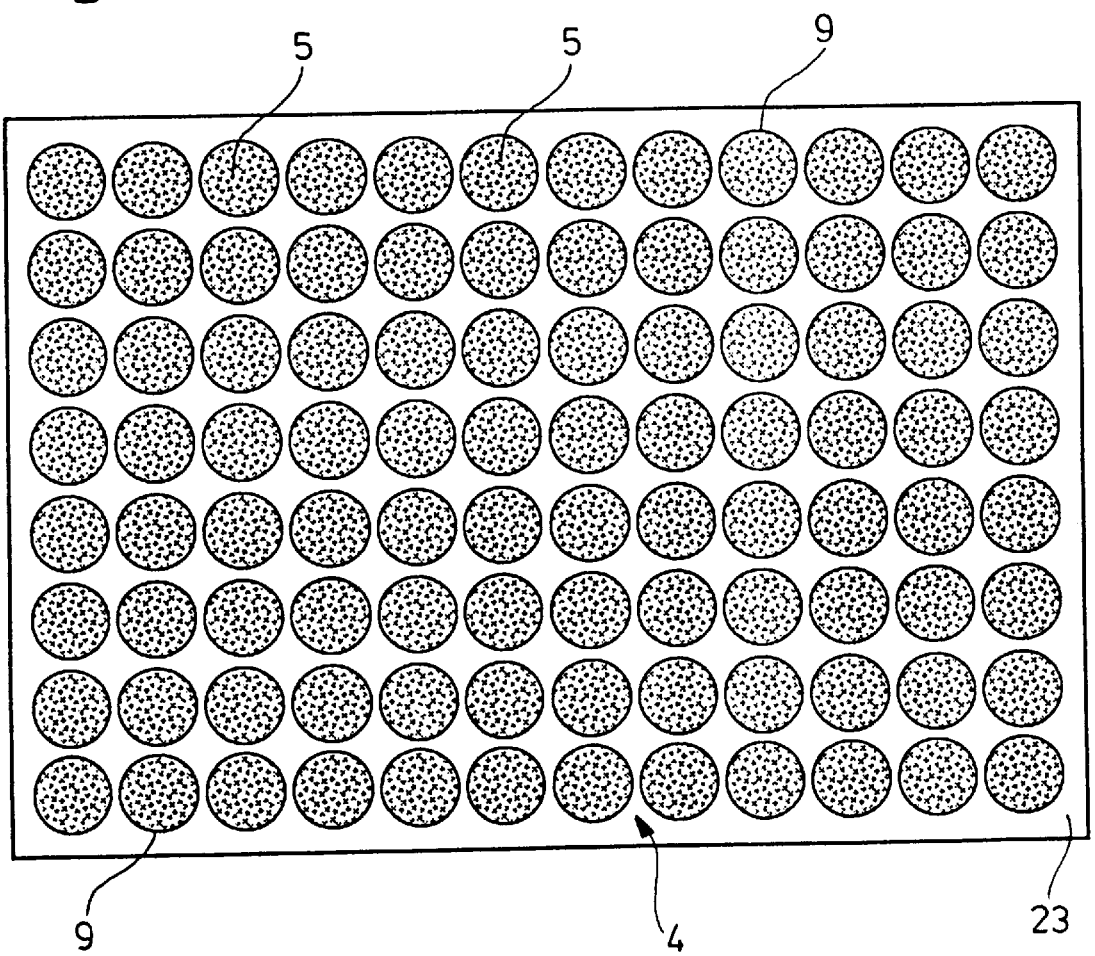
Figure 5:
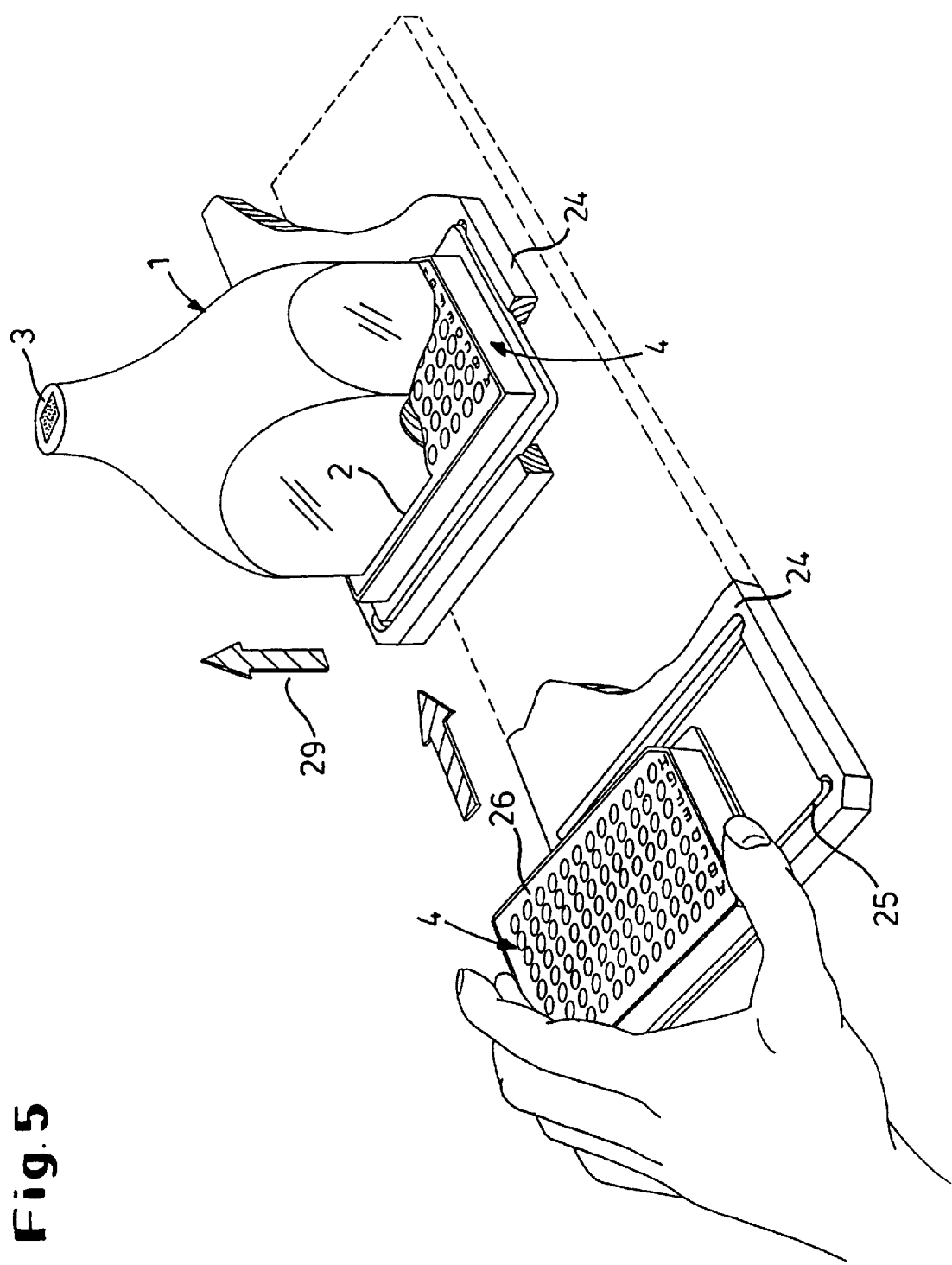
Figure 6:
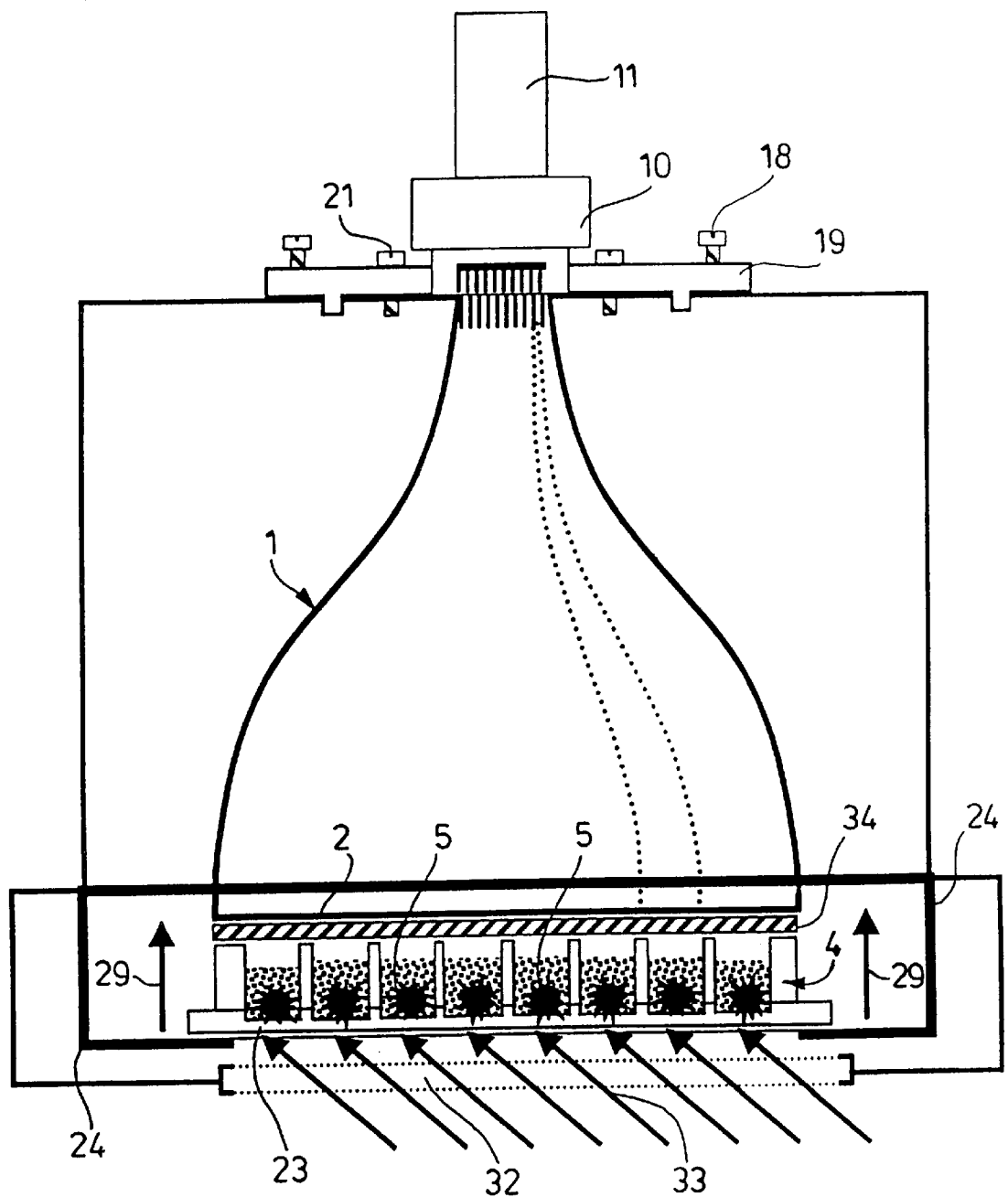
Figure 7:
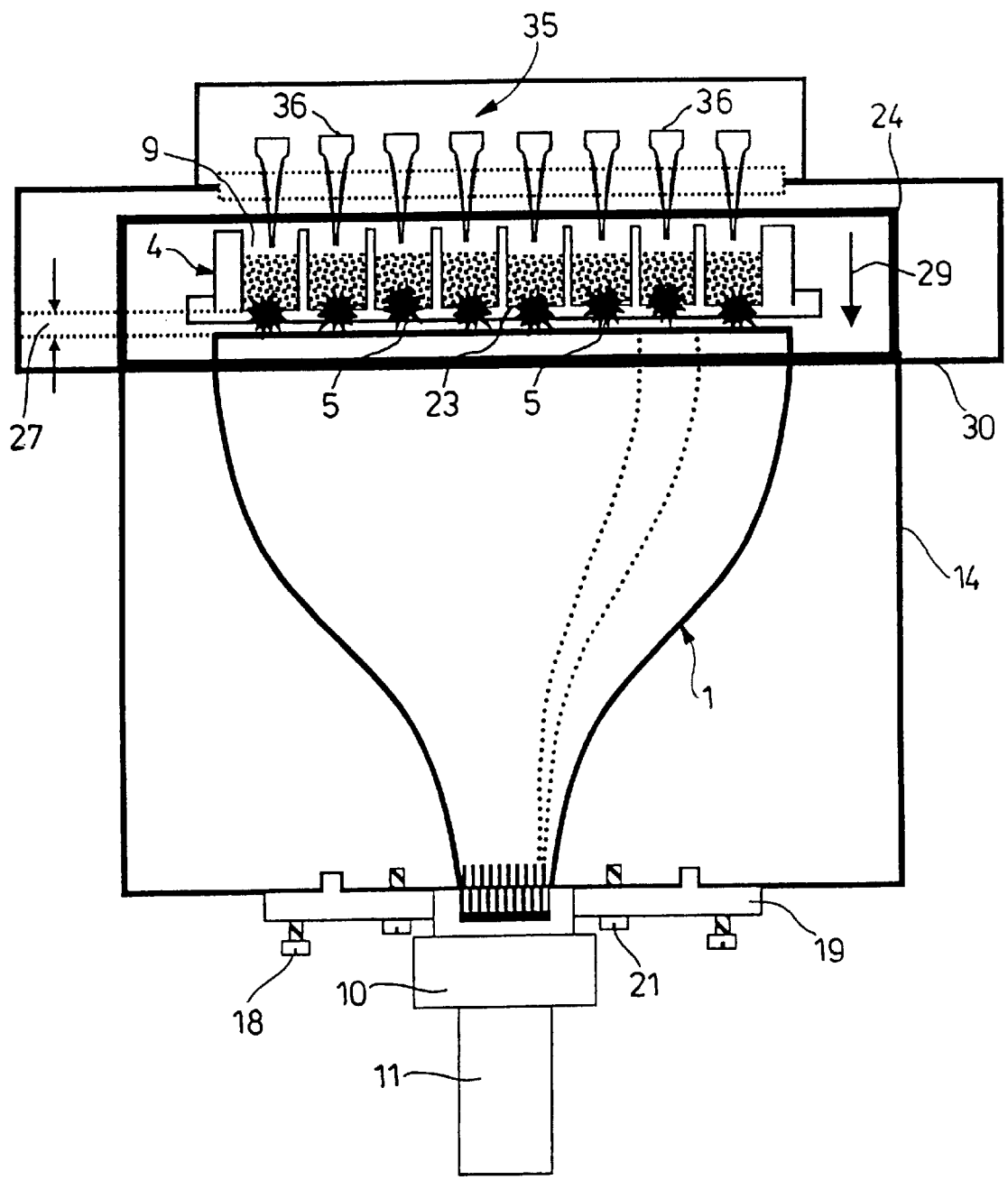

FIG. 2b shows a diagrammatic view of the luminescence measurement system in a position (BOTTOM position) rotated through 180° relative to FIG. 2a FIG. 3 shows the structure of the measurement system for luminescent biological objects FIG. 4 shows a plan view of a microtitre plate FIG. 5 shows the drawer-like mount of the microtitre plate FIG. 6 shows the fundamental structure of a measurement system for investigating fluorescent biological objects with excitation light of inclined incidence FIG. 7 shows the fundamental structure of a luminescence measurement system in the BOTTOM position with a pipetting device for investigating dynamic processes in luminescent biological objects.

The invention utilizes the property of optical waveguides (glass or polymer fibres) of transmitting light signals, in particular including individual photons, in a wide spectral range. An ordered arrangement of a large number of fibres in an xy area makes it possible to display a brightness image as intensity raster graphic at another location (image conductor). For this purpose, each point xgi, ygi in the object plane g must correspond to a point xbi, ybi in the image plane b. If each fibre of the image conductor is geometrically tapered on its path from the object plane to the image plane by its diameter being reduced, then the object image is reduced by the Factor=fibre diameter (object plane)/fibre diameter (image plane), or magnified, if object and image planes are interchanged. This imaging element based on optical waveguides is referred to below as optical taper arrangement or taper element. Such elements are manufactured industrially as optical image transmission elements. Worldwide there are two manufacturing companies able to process large-area taper elements, that is to say glass-fibre bundles up to a diameter of 147 mm, and produce them in accordance with customer specifications with regard to the desired scale of reduction. An important optical imaging property is that both on the object side (large end surface of the taper element) and on the image side (small end surface of the taper element), the individual glass fibres are parallel to the optical axis and are thus directed perpendicularly into or onto the signal-generating test objects, thereby avoiding the disturbing vignetting effects (parallax errors) occurring in the case of lens imaging.

The input windows of the image intensifier photocathodes of commercial photon counting systems have a diameter of 12 mm, 18 mm, 25 mm or 40 mm. As the area becomes larger, the price of the image intensifiers increases more than proportionally. On the other hand, a minimum reduction factor fv is to be sought for the taper element because its aperture and hence its performance in the transmission of optical signals decreases at 1/fv. In the case of the present invention, an image intensifier with a diameter of 25 mm was selected as an acceptable compromise between costs and usefulness. This results in a computational numerical aperture of 0.167 in accordance with an aperture angle of approximately 20 degrees in comparison with the much smaller aperture angle of an f 1:1.0 objective at a distance of 70 cm of 0.1 degree.

Owing to this aperture angle of the glass-fibre optical arrangement being greater than in the case of lens/mirror imaging systems, the photon collecting property is improved with the aid of the taper element by a multiple relative to the conventional optical arrangement. Comparative measurements with the best known photon counting system, equipped first of all with an optical lens arrangement (Leica Noctilux f 1:1.0) and secondly with the optical taper arrangement, prove a sensitivity increase of 1000%. The sensitivity of a system for the transmission of optical signals was able to be increased by the factor of 10 with the aid of the optical imaging arrangement comprising the glass-fibre taper element.

Figure 1:
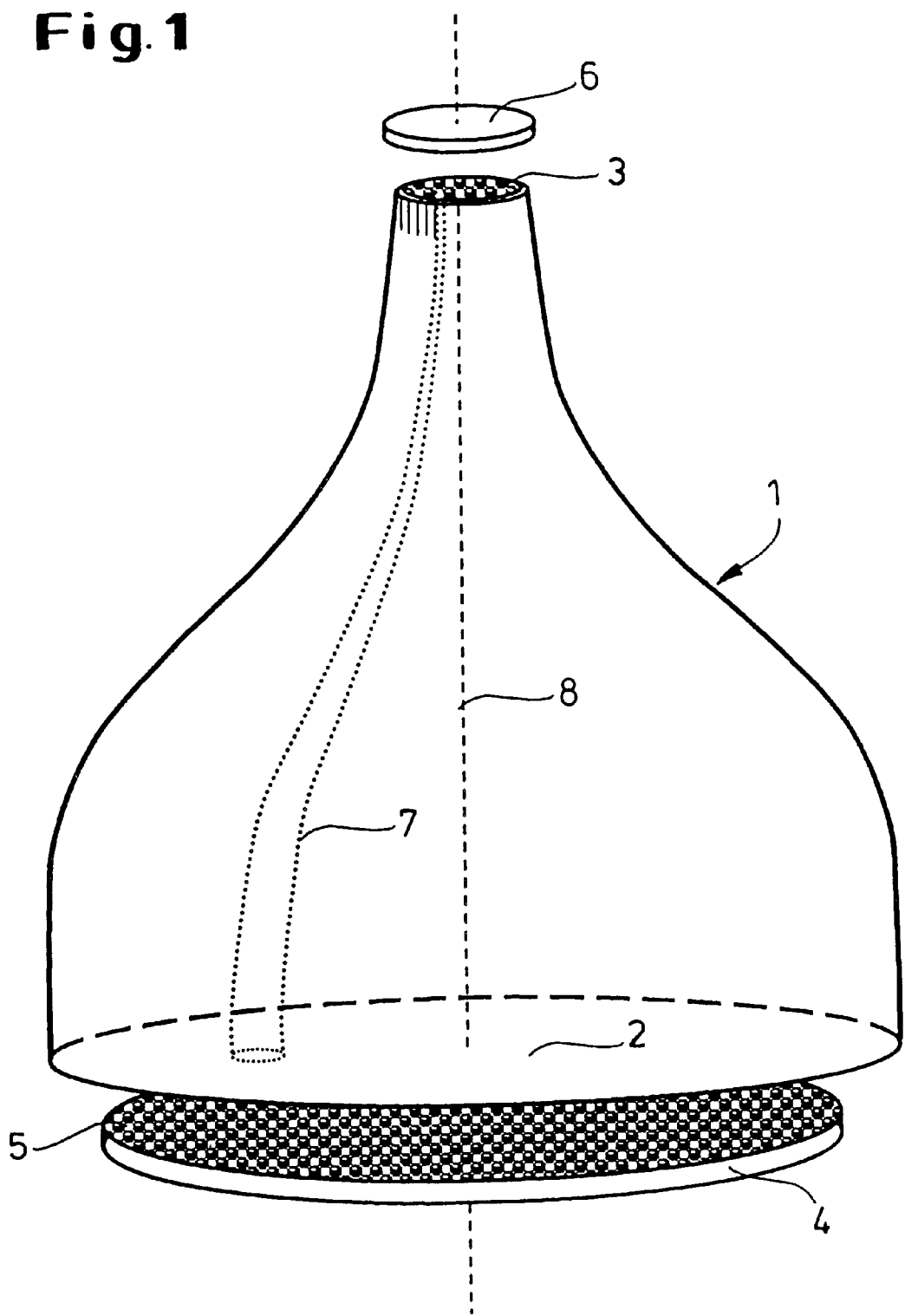
FIG. 1 shows the fundamental structure of the optical measurement system

The fundamental structure of the optical measurement system is evident in FIG. 1. The most important component in this case is the glass-fibre taper element 1 having a large-area end 2 and a small-area end 3. Situated opposite the large end surface 2 is a planar carrier 4 with the test objects 5 arranged thereon, and situated opposite the small end surface 3 is an image sensor 6 for the acquisition and further processing of the reduced image of the carrier surface with the test objects 5. The taper element 1 has approximately a bell-shaped contour. Both at the large end surface 2 and at the small end surface 3, the individual glass fibres 7 are oriented parallel to the optical axis 8 and thus perpendicular to the respective surfaces 2 and 3.

A pivotable luminescence measurement system is illustrated according to FIGS. 2a and 2b. In this case, the carrier 4 is a microtitre plate with test holes 9 for the objects 5 to be investigated. The measurement system essentially comprises the microtitre plate 4, the glass-fibre taper element 1, an image intensifier 10 and a CCD camera 11. The entire system is fitted on a fixed frame 13 in a manner allowing it to pivot about a horizontal rotary spindle 12. The taper element 1 is accommodated in a light-tight housing 14. The position according to FIG. 2a corresponds to the basic position, in which the microtitre plate 4 is arranged as the lowest component and the optical elements 1, 10, 11 are arranged above it. This position corresponds to the so-called TOP measurement position. In contrast to this, the entire system is pivoted through 180° about the rotary spindle 12 in the position according to FIG. 2b. In this case, the microtitre plate 4 is situated right at the top and, consequently, is also accessible from the top, while the optical components 1, 10, 11 are situated below the microtitre plate 4. This position corresponds to the so-called BOTTOM measurement position. In the case of pivoting through 180 degrees, therefore, the light-tight housing 14 is rotated with the taper element 1 as optical reduction arrangement and the flanged-on photo detection system 10, 11 as rigid unit. The large-area end of the taper element 1 faces the microtitre plate 4 and its small-area end faces the image intensifier 10. The reduction factor of the taper element 1 is selected such that the reduced image of the microtitre plate 4 fully fills the entry window of the image intensifier 10. A reduction factor in the range from 1:2 to 1:6 is to be regarded as optimum in the case of measurement systems of this type.

The actual structure of the optical system is evident in FIG. 3, in which the TOP position is again illustrated. In the course of setting up and adjusting the system, it is necessary for the glass-fibre entry window 15 on the image intensifier 10 to be brought into contact with the small-area end 3 of the taper element 1 in order to ensure that the photons on the taper output side are efficiently transferred to the photocathode 16 of the image intensifier 10.

When white plastic carriers are used, e.g. white microtitre plates, an image intensifier having a bialkali photocathode is expediently resorted to, because the specific spectral sensitivity of such a photocathode prevents the negative property (associated with all white microtitre plates) of light-induced long-term photophorescence, which principally occurs at approximately 800 mm, from bringing about an unidentifiable false light signal and hence sensitivity limitation. Since the spectral sensitivity of the bialkali photocathode is virtually zero above 700 nm, the false light originating from the long-term phosphorescence is suppressed.

The gap 17 between taper element 1 and the input window 15 can be brought to a distance of zero in the z direction by means of adjusting screws 18 on the camera carrier plate 19. In this case, a spreading drop of oil 20 introduced into the gap 17 minimizes the reflection losses by matching the refractive index during the transition from the taper element 1 to the detection system 10, 11. In this case, the oil has the same refractive index as the glass of the taper element 1. A rigid connection between the taper element 1 and the image intensifier 10 is established by the locking screws 21, which connection is light-tight by means of a light trap 22.

The microtitre plate 4 (also see FIG. 4) has a multiplicity of cylindrical or rectangular test holes 9 (so-called wells) for receiving the luminescent biological objects 5. As a special design for the BOTTOM arrangement (in accordance with FIG. 2b), the base 23 of the microtitre plate 4 is composed of an optically transparent material.

The mount in the form of a drawer for the microtitre plate 4 is explained in more detail with reference to FIG. 5. The measurement apparatus is loaded with the microtitre plate 4 with the aid of an extendable drawer 24, which is designed in such a way that it can receive the microtitre plates 4 in an open frame construction 25 at least for the BOTTOM measurement method, so that the actual measurement surface is not covered. The extending of the drawer 24 is coupled with an interruption of the high voltage of the image intensifier 10, in order to protect the latter against destruction by too much light. When the microtitre plate 4 is retracted, a gap 27 of a few millimeters initially remains between its surface 26 and the large-area (in this case lower) taper surface 2 (see FIG. 3), in order to avoid bumping during the retraction operation and hence possible damage to the taper surface 2. In order to fulfil the conditions for optimum signal input coupling with optimum spatial resolution, the microtitre plate surface 26 and the taper surface 2 have to be brought into contact. This is done by means of a resilient vertical adjustment 29 (only indicated diagrammatically in FIGS. 3 and 5), by means of which the microtitre plate 4 is raised against the taper element 1 after the microtitre plate 4 has been positioned precisely under the large end surface 2 of the taper element 1, which surface yields, however, after a defined pressure force is exceeded. This enables microtitre plates 4 with different height dimensions to be adapted to the taper surface 2 without any play. The base of the housing part 30 enclosing the drawer 24 contains a perforation which can be closed off by a dummy plate 31 (see FIG. 3).

According to FIG. 6, the dummy plate is removed and replaced by a window 32. Fluorescent excitation light 33 can be radiated in through this window at an inclined angle of incidence in the TOP measurement position in order to be able to investigate fluorescent objects. In this arrangement, the base 23 of the microtitre plate 4 is likewise optically transparent. An exchangeable, large-area interference filter 34, which is selective for the fluorescent light, is arranged between the large end surface 2 of the taper element 1 and the microtitre plate 4 in order to suppress interfering radiation from the excitation light 33. Consequently, the apparatus described can be converted quickly and without difficulty from a luminescence measurement system to a fluorescence measurement system having the same high sensitivity.

A further possibility for expansion of the luminescence measurement system is illustrated in FIG. 7. The apparatus, which is in this case pivoted into the BOTTOM measurement position, is additionally equipped with a micropipetting system 35, which is arranged above the microtitre plate 4. In this case, the individual pipettes 36 are assigned to the individual test holes 9 (wells) of the microtitre plate 4. As in the case of the design described above, the drawer-like mount 24 for the microtitre plate 4 is provided with a frame 25 (see FIG. 5) in order that the top side of the microtitre plate 4 is accessible for the micropipetting system 35 and the underside is accessible for observation of the luminescence. The base 23 of the microtitre plate 4 is once again composed of an optically transparent material in order to observe the luminescent radiation of the samples 5 from the underside through the base 23. This expansion permits dynamic investigation of luminescent biological objects, e.g. under the influence of reaction liquids which can be fed in via the pipettes 36. Kinetic bioluminescence investigations having a temporal resolution of 40 ms (video standard) which reflect the dynamic action profile of pharmacologically active substances on the biological objects are possible in this way. In the case of rapidly decaying luminescence reactions of the biological system of the order of magnitude of a few hundred ms to 2 s, substance effects can be investigated only in this way.

What is claimed is:

1. Measurement system for detecting optical signals of microassays, in which the signal-generating test objects (5) are arranged on an investigation surface of a planar carrier (4), comprising an optical imaging arrangement which reduces the size of the test objects (5) to be measured in such a way that all the objects are imaged completely on a two-dimensional, photosensitive image sensor (6), characterized in that the optical imaging arrangement comprises a high-resolution glass-fibre taper element (1) having a large-area (2) and a small-area end (3) and the end surfaces (2, 3) are chosen such that the large-area end surface (2) corresponds at least to the investigation surface of the carrier (4) and the small-area end surface (3) corresponds to the size of the image sensor (6), the ratio of the end surfaces (2, 3) producing the scale of reduction of the optical imaging arrangement in order to image the investigation surface of the carrier (4) completely onto the image sensor (6) wherein the planar carrier comprises a plate (4) having a multiplicity of holes (9) for receiving the signal-generating test objects (5), in that the image sensor (6) comprises an image intensifier (10) and a video camera (11) for converting the intensified image signals into electronic signals, and in that the glass-fibre taper element (1) generates a reduced image of the plate (4) that fully fills the entry window (15) of the image intensifier (10).

2. Measurement system according to claim 1, wherein the image intensifier (10) has a bialkali photocathode whose spectral sensitivity at wavelengths>700 nm is<1%.

3. Measurement system according to claim 1, wherein the plate (4) is arranged in a horizontally movable and vertically adjustable, drawer-like mount (24), which, after horizontal retraction, is raised to an extent such that the large-area end (2) of the glass-fibre taper element (1) is in direct contact with the surface of the plate (4).

4. Measurement system according to claim 1, wherein the small-area end (3) of the glass-fibre taper element (1) is in direct optical contact with the entry window (15) of the image intensifier (10).

5. Measurement system according to claim 1, wherein the entry window (15) of the image intensifier (10) is formed by a glass-fibre plate which transfer the image directly onto the photocathode (16) of the image intensifier (10) situated behind it.

6. Measurement system according to claim 1, wherein in order to minimize reflection losses, an air gap (17) remaining between the glass-fibre taper element (1) and the entry window (15) of the image intensifier (10) is filled with an oil film (20), whose refractive index corresponds to the refractive index of the taper element (1).

7. Measurement system according to claim 1, wherein the plate (4) has an optically transparent base (23), in that the drawer-like mount (24) is designed as a frame construction (25) and in that a light source for fluorescence excitation which generates a light pencil (33) of inclined incidence with respect to the optical axis is arranged underneath the plate (4).

8. Measurement system according to claim 1, wherein the entire apparatus can be pivoted through 180° about a horizontal spindle (12) and has the following further features:

a) the plate (4) has an optically transparent base (23), b) the drawer-like mount (24) for the plate (4) is designed as a frame construction (25), c) the measurement system additionally has a pipetting system (35) whose individual pipettes (36) are assigned to the test holes (9) in the plate (4).

9. Measurement system according to claim 1, wherein said plate (4) is a microtitre plate.

* * * * *